| United States Patent [19] | [11] | 4,203,220 |
|---|---|---|
| Cranfield | [45] | May 20, 1980 |

[54] NEW TRIAZINES AND THEIR USE IN BONDING RESINS TO BIOLOGICAL TISSUE

[75] Inventor: Peter J. Cranfield, London, England

[73] Assignee: National Research Development Corporation, London, England

[21] Appl. No.: 703,660

[22] Filed: Jul. 8, 1976

[30] Foreign Application Priority Data

Jul. 9, 1975 [GB] United Kingdom ............... 28927/75

[51] Int. Cl.$^2$ .............................................. A61K 5/06
[52] U.S. Cl. ..................................... 433/228; 525/78; 525/80; 526/248; 526/261; 544/191; 433/191; 433/201

[58] Field of Search .................... 32/15, 2; 525/78, 80; 544/194; 526/248, 261

[56] References Cited

U.S. PATENT DOCUMENTS

| 3,987,546 | 10/1976 | Trampe | 32/2 |
| 4,155,890 | 5/1979 | Von Nostizt | 260/23 AR |

Primary Examiner—Lester L. Lee
Attorney, Agent, or Firm—Cushman, Darby & Cushman

[57] ABSTRACT

New alkenylamino dihalo triazines are used as bridging molecules to facilitate bonding of clinically tolerated acrylic and similar resins to biological tissue such as teeth and bone.

12 Claims, No Drawings

NEW TRIAZINES AND THEIR USE IN BONDING RESINS TO BIOLOGICAL TISSUE

This invention relates to bonding of polymeric materials to biological tissue, in particular to hard biological tissue such as dental enamel, dentine or bone.

Present methods of bonding dental resins to dental tissue rely upon mechanical bonding and upon adhesive bonding, polar molecules within the adherand being adsorbed onto the surface of the biological tissue. In most cases the inorganic apatitic and crystalline portion of the tissue acts as the adsorbent surface. Under these conditions of bonding it has been found that whilst good initial bonding can be made to dental enamel, bonding to dentine is very poor, and in fact almost non-existent. Treatment of the biological tissue with silanes of phosphonates does not improve this bonding to the required degree.

A method of bonding dental resins to dental tissue has now been discovered which involes the use of a novel bifunctional bridging molecule which has a group that can react chemically with the dental tissue, particularly the dentine, and a reactive group that can copolymerise with the dental resin.

The present invention provides a compound of the general formula:

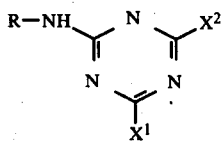

wherein R is an organic group containing a polymerisable olefinic double bond and $X^1$ and $X^2$ which may be the same, or different, each represent F or Cl or Br.

The group R is preferably an alkenyl group of 3 to 6 carbon atoms e.g. an allyl group. Preferred reactive substances of formula (I) are 2-N'-allylamino-4,6-dichloro-1,3,5-triazine and 2-N'-allylamino-4,6-difluoro-1,3,5-triazine.

The compounds of formula (I) can be prepared by reacting a compound of formula:

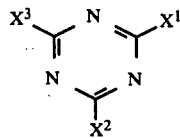

wherein $X^1$ and $X^2$ are as defined above and $X^3$ if F,Cl or Br with an equimolar amount of an amine of formula $R-NH_2$, wherein R is as defined above.

Dental resins are usually acrylic materials based on an ester of acrylic or methacrylic acid, typical monomers being methyl methacrylate or a diacrylate of 2,2-bis-(p-hydroxyphenyl)-propane, known as BIS-(GMA) resins. The dental resin is normally used as a monomer or as a monomer/polymer mixture i.e. an incompletely polymerised resin and polymerisation is completed in situ when the resin has been placed in position on the dental tissue. Other types of clinically tolerated resins are known and used e.g. in dentistry or orthopaedic surgery, all of which have polymerisable olefinic double bonds in the molecule. All such resins are available as monomers or monomer/polymer mixtures and include any necessary catalysts etc. so that, after the resin has been put in its final position, completion of polymerisation occurs within a few minutes under ambient conditions.

In using the bifunctional bridging molecule I in accordance with the present invention, the bifunctional molecule I can either be reacted first with the resin and the modified resin used on the biological tissue so that chemical bonding takes place, or preferably, the biological tissue is treated first with the bifunctional molecule I and the treated tissue then contacted with conventional dental resin.

The present invention therefore provides a method of bonding a clinically tolerated resin having polymerisable olefinic double bonds to biological tissue which comprises bringing the bifunctional molecule I into contact with biological tissue under conditions whereby the compound becomes chemically bonded to the tissue and subsequently bringing an incompletely polymerised resin into contact with the biological tissue to which the compound is bonded and completing the polymerisation of the resin under conditions such that the resin copolymerises with the olefinic double bond in compound I.

The bonding of the bifunctional molecule I to the tissue, normally a proteinaceous tissue such as dental enamel or dentine, or bone occurs by reaction between one of the fluoro, chloro or bromo groups on the triazine ring and a reactive group e.g. amino or hydroxy, which is always present on the surface of the tissue. The reaction produce of the bifunctional molecule I with biological tissue is a novel material forming a further aspect of the present invention.

The present invention also provides a method of bonding a clinically tolerated resin having polymerisable olefinic double bonds to biological tissue which comprises bringing a mixture or a copolymer of (1) the bifunctional molecule I and (2) the resin into contact with the tissue under conditions whereby $X^1$ or $X^2$ reacts with the tissue and the polymerisation of the resin is completed. The mixture or copolymer used in this method form a further aspect of the invention.

In this last mentioned variant of the method, the olefinic double bond in the bifunctional molecule I may copolymerise with the olefinic double bonds in the resin before or after it is brought into contact with the tissue and the polymerisation of the resin is completed and any copolymerisation of the bifunctional molecule I necessary completed in the final stages of resin curing when the resin is in its final position on the tissue. At the same time, group $X^1$ or $X^2$ originating from bifunctional molecule I reacts with reactive groups e.g. amino or hydroxy, on the surface of the tissue to complete the bonding of the resin molecules to the tissue via the bifunctional molecule I.

When bifunctional molecule I is to be applied directly to dental tissue, it is convenient to apply a solution of the bifunctional molecule in an organic solvent e.g. acetone, or an aqueous solvent e.g. aqueous acetone, to the dental tissue. A conventional dental resin can then be used e.g. in restorative work, to form restorations or other dental work showing a much stronger bonding to the dental tissue than was previously available with dental resins of that particular type.

The following Example illustrates the invention:

Trichloro-s-triazine (cyanuric chloride: 1.85 g) was dissolved in warm acetone (6 ml) and the resulting solution was added to ice water (10 ml) to form a slurry. The slurry was cooled to 0°–5° C. and 3-aminopropane (allylamine; 0.6 g.; 0.81 ml) was added dropwise, followed by sodium bicarbonate (0.9 g). The slurry obtained was filtered, washed with water and dried. Recrystallisation of the dried solid from 40°/60° C. petroleum ether gave the mono allylamino-substituted triazine of formula:

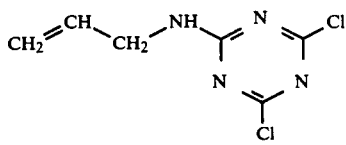

When a solution of this material in acetone is applied to freshly cut dentine or dental enamel, at body temperature, a second chlorine atom on the triazine ring is displaced as the triazine reacts with amino, hydroxyl and/or other chemical groups within the organic phase of the dentine or enamel. The triazine derivative is thus bound to the biological tissue and the free vinyl group of the 3-amino propene is able to take part in a polymerisation of a dental resin on the biological surface to form. e.g. (poly)methylmethacrylate. The polymer formed is firmly bound to the biological tissue.

The tensile bond strength between a dental resin and dentine was measured using an Instron tensile testing machine. The tests were carried out on extracted human teeth which were cut and ground to expose a smooth dentine surface. The resin used was a polymethylmethacrylate dental resin which, in control experiments, was applied directly to the freshly exposed dentine surface. The dental resin cures within 5 minutes and the tooth, to which the resin is bonded, was aged for three days in water at 37° C. After this aging, the tensile bond strength between the resin and the dentine was measured and found to be in the range 2.0 to 7.5 kg/cm$^2$.

The above experiment was repeated, but prior to bringing the resin into contact with the dentine, the freshly exposed dentine was painted with an acetone solution saturated with 1,3,-dichloro-5-allylamino triazine. The acetone was allowed to evaporate and the treated dentine surface then covered with the resin. After aging as described above, the tensile bond strength was found to be in the range 9–55 kg/cm$^2$.

I claim:

1. A method of bonding a clinically tolerated resin having polymerisable olefinic double bonds to a surface of a biological tissue which comprises contacting the biological tissue with a compound of the general formula

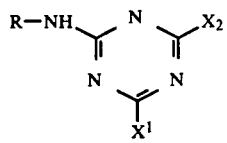

wherein R is an organic group containing a polymerisable olefinic double bond and $X^1$ and $X^2$ independently represent F or Cl or Br so as to react at least one of $X^1$ and $X^2$ with a reactive group present on the surface of the biological tissue to form a reaction produce containing a group R, contacting the resin with the reaction product and copolymerising the resin with the olefinic double bond in the group R in the reaction product.

2. A method of bonding a clinically tolerated resin having polymerisable olefinic double bonds to a surface of a biological tissue which comprises contacting a compound of the general formula

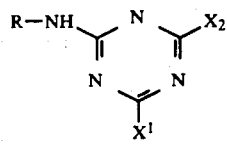

wherein R is an organic group containing a polymerisable olefinic double bond and $X^1$ and $X^2$ independently represent F or Cl or Br, with a clinically tolerated resin having polymerisable olefinic double bonds to form a mixture of the compound and the resin or to form a copolymer of the compound and the resin, and then contacting the mixture or copolymer with the biological tissue so that at least one of the groups $X^1$ and $X^2$ reacts with a reactive group present on the surface of the biological tissue and the polymerisation of the resin is completed.

3. A method according to claim 1 or 2 wherein R is an alkenyl group of 3 to 6 carbon atoms and $X^1$ and $X^2$ are F or Cl.

4. A method according to claim 1 or 2 wherein R is an allyl group and $X^1$ and $X^2$ are both Cl.

5. A method according to claim 1 or 2 wherein the resin is a dental resin comprising monomeric or a mixture of monomeric and polymeric methyl methacrylate or monomeric or a mixture of monomeric and polymeric diacrylate ester of 2,2-(bis-p-hydroxyphenyl)-propane.

6. A method according to claim 3 wherein the resin is a dental resin comprising monomeric or a mixture of monomeric and polymeric methyl methacrylate or monomeric or a mixture of monomeric and polymeric diacrylate ester of 2,2-(bis-p-hydroxyphenyl)-propane.

7. A reaction product of a biological tissue containing a reactive group on its surface with a compound of the general formula

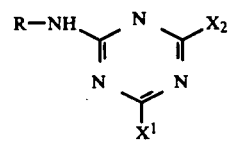

wherein R is an organic group containing a polymerisable olefinic double bond and $X^1$ and $X^2$ independently represent F or Cl or Br.

8. A method according to claim 1 or 2 wherein the biological tissue is dental enamel, dentine or bone.

9. A reaction product according to claim 7 wherein the biological tissue is dental enamel, dentine or bone.

10. A reaction product according to claim 7 which is a reaction product of the biological tissue with a mixture of the triazine compound and a clinically tolerated resin having polymerisable olefinic double-bonds.

11. A reaction product according to claim 10 wherein the resin is a dental resin comprising monomeric or a mixture of monomeric and polymeric methyl methacrylate or monomeric or a mixture of monomeric and polymeric diacrylate ester of 2,2-(bis-p-hydroxyphenyl)-propane.

12. A method according to claim 4 wherein the resin is a dental resin comprising monomeric or mixture of monomeric and polymeric methyl methacrylate or monomeric or a mixture of monomeric and polymeric diacrylate ester of 2,2-(bis-p-hydroxphenyl)-propane.

* * * * *